US00PP12950P2

(12) United States Plant Patent
Bergman

(10) Patent No.: US PP12,950 P2
(45) Date of Patent: Sep. 10, 2002

(54) CHRYSANTHEMUM PLANT NAMED 'PINK YOGRACELAND'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 11 days.

(21) Appl. No.: 09/829,489

(22) Filed: Apr. 11, 2001

(51) Int. Cl.[7] ..... A01H 5/00
(52) U.S. Cl. ..... Plt./297
(58) Field of Search ..... Plt./286, 297

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4): 138–142.*

Broertjes, et al., 1980, "A mutant of a . . . Irradation of progressive radiation induced mutants in a mutation breeding programme with *Chrysanthemum morifolium,*" Ephytica 29:525–530.*

Gosling, ed., "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods In the Improvement of Vegetatively Propagated Crops", Elsevier Sci. Pub. Co., New York, pp. 162–175.*

Searle, et al., 1968, "Chrysanthemums the Year Round", Blanford Press, London, pp. 27–29, 320–327.*

Chan, 1966, "Chrysanthemum and rose mutations induced by X–rays", Am. Soc. Hort. Sci. Proc., pp. 613–620.*

Broertjes, 1966, "Mutation breeding of chrysanthemums", Euphytica, 15:156–162.*

Dowrick, et al., 1966, "The induction of mutations in Chrysanthemum using X– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Pink Yograceland', characterized by its uniform and upright plant habit; strong, dark green foliage; uniform flowering response; early flowering; very large daisy-type inflorescences with large anemone centers; lavender pink-colored ray and bright yellow-colored disc florets; and good post-production longevity.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Pink Yograceland'.

The new Chrysanthemum is a product of a planned breeding program conducted by the Inventor in Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum is a naturally-occurring whole plant mutation of a proprietary induced mutation that originated by exposing unrooted cuttings of the Chrysanthemum cultivar Yograceland, disclosed in U.S. Plant Pat. No. 12,512, to X-ray radiation in October, 1998, in Fort Myers, Fla. The new Chrysanthemum was discovered and selected by the Inventor as a single flowering plant within a population of plants of the irradiated selection in April, 1999 in Fort Myers, Fla. The selection of this plant was based on its uniform plant growth habit, good vigor, desirable inflorescence form and floret colors, fast response time, and good postproduction longevity.

Asexual reproduction of the new Chrysanthemum by vegetative tip cuttings was first conducted in Fort Myers, Fla. in July, 1999. Asexual reproduction by cuttings has shown that the unique features of this new Chrysanthemum are stable and reproduced true to type in successive generations.

SUMMARY OF THE INVENTION

The cultivar Pink Yograceland has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Pink Yograceland'. These characteristics in combination distinguish 'Pink Yograceland' as a new and distinct Chrysanthemum:

1. Uniform and upright plant habit.
2. Strong, dark green foliage.
3. Uniform flowering response.
4. Can be grown as a disbud or as a spray-type.
5. Early flowering, eight-week response time.

6. Very large daisy-type inflorescences that are about 14.5 cm in diameter with large anemone centers.
7. Lavender pink-colored ray and bright yellow-colored disc florets.
8. Good postproduction longevity with plants maintaining good substance and color for about three or four weeks in an interior environment.

Plants of the new Chrysanthemum can be compared to plants of the cultivar Yograceland. In side-by-side comparisons conducted by the Inventor in Salinas, Calif., plants of the new Chrysanthemum differ from plants of the cultivar Yograceland in the following characteristics:

1. Plants of the new Chrysanthemum flower slightly later than plants of the cultivar Yograceland.
2. Ray and disc florets of plants of the new Chrysanthemum are darker in color than ray and disc florets of plants of the cultivar Yograceland.

Plants of the new Chrysanthemum can be compared to plants of the Chrysanthemum cultivar Yohartford, disclosed in U.S. Plant Pat. No. 12,513. In side-by-side comparisons conducted by the Inventor in Salinas, Calif., plants of the new Chrysanthemum differ from plants of the cultivar Yohartford in the following characteristics:

1. Plants of the new Chrysanthemum are more vigorous and larger than plants of the cultivar Yohartford.
2. Plants of the new Chrysanthemum have larger inflorescences than plants of the cultivar Yohartford.
3. Ray florets of plants of the new Chrysanthemum are lighter pink than ray florets of plants of the cultivar Yohartford.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a top perspective view of a typical flowering plant of 'Pink Yograceland' grown a disbud-type.

The photograph at the top of the second sheet comprises a close-up view of typical inflorescences of 'Pink Yograceland' grown as a disbud-type.

The photograph at the bottom of the second sheet comprises a close-up view of typical inflorescences of the new Chrysanthemum (left) and 'Yograceland' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as disbud types. Measurements and numerical values represent averages of typical flowering plants.

Botanical classification: *Chrysanthemum×morifolium* cultivar Pink Yograceland.

Commercial classification: Daisy-type potted Chrysanthemum with anemone centers.

Parentage: Naturally-occurring whole plant mutation of a proprietary *Chrysanthemum×morifolium* induced mutation, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum with anemone centers that can be grown as a disbud-type or as a spray-type. Stems mostly upright and somewhat ourwardly spreading; uniform crown. Freely branching, about four lateral branches develop after removal of terminal apex (pinching); dense and full plants.

*Plant height.*—About 23.5 cm.

*Plant width.*—About 37.5 cm.

*Lateral branches.*—Length: About 17.5 cm. Diameter: About 4 mm. Internode length: About 1.4 cm. Strength: Strong. Texture: Pubescent. Color: Close to 146A.

*Foliage description.*—Arrangement: Alternate. Quantity of leaves per lateral stem: About 10 or 11. Length: About 6.8 cm. Width: About 5.7 cm. Apex: Rounded, cuspidate to mucronate. Base: Attenuate to truncate. Margin: Palmately lobed, sinuses between lateral lobes divergent. Texture: Upper and lower surfaces with very fine pubescence; veins prominent on lower surface. Color: Young foliage, upper surface: 147A. Young foliage, lower surface: Close to 147B. Mature foliage, upper surface: 147A. Mature foliage, lower surface: Close to 147B. Venation, upper surface: 147A to 147B. Venation, lower surface: 147B. Petiole length: About 2.6 cm. Petiole diameter: About 3 mm. Petiole color: Close to 146B.

Inflorescence description:

*Appearance.*—Daisy-type inflorescence form with elongated oblong-shaped ray florets and large anemone centers. Inflorescences borne on terminals above foliage. Disk and ray florets arranged acropetally on a capitulum. Not fragrant. Can be grown as a disbud or as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 47 to 51 days later when grown during the winter.

*Postproduction longevity.*—Inflorescences maintain good color and substance for about three or four weeks in an interior environment.

*Quantity of inflorescences.*—Produced as a disbud-type, all the lateral inflorescences are removed leaving only the terminal inflorescence.

*Inflorescence bud.*—Height: About 9 mm. Diameter: About 1.1 cm. Color: Close to 143A.

*Inflorescence size.*—Diameter: About 14.5 cm. Depth (height): About 2.6 cm. Diameter of disc: About 5.1 cm. Receptacle diameter: About 9 mm.

*Ray florets.*—Shape: Elongated-oblong. Orientation: Initially upright, then perpendicular to the peduncle. Aspect: Slightly reflexed and slightly twisting. Length: About 7.3 cm. Width: About 1.75 cm. Corolla tube length: About 2 mm. Apex: Mostly acute, occasionally emarginate. Base: Attenuate; very short corolla tube. Margin: Entire. Texture: Smooth, glabrous, satiny. Number of ray florets per inflorescence: About 25 arranged in a single row. Color: When opening and fully opened, upper surface: 75A to 75B. When opening and fully opened, lower surface: 75C to 75D.

*Disc florets.*—Arrangement: Massed at center of receptacle, enlarged. Shape: Tubular, elongated. Apex: Five-pointed. Length: About 2.5 cm. Width: Apex: About 7 mm. Base: About 2 mm. Number of disc florets per inflorescence: About 177. Color: Immature: 144A to 154A. Mature: Apex: 5A. Mid-section: 4D to 155A with longitudinal stripes, 5A. Base: 5A.

*Reproductive organs.*—Androecium: Present on disc florets only. Anther color: 12A. Pollen: None observed. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Pink Yograceland', as illustrated and described.

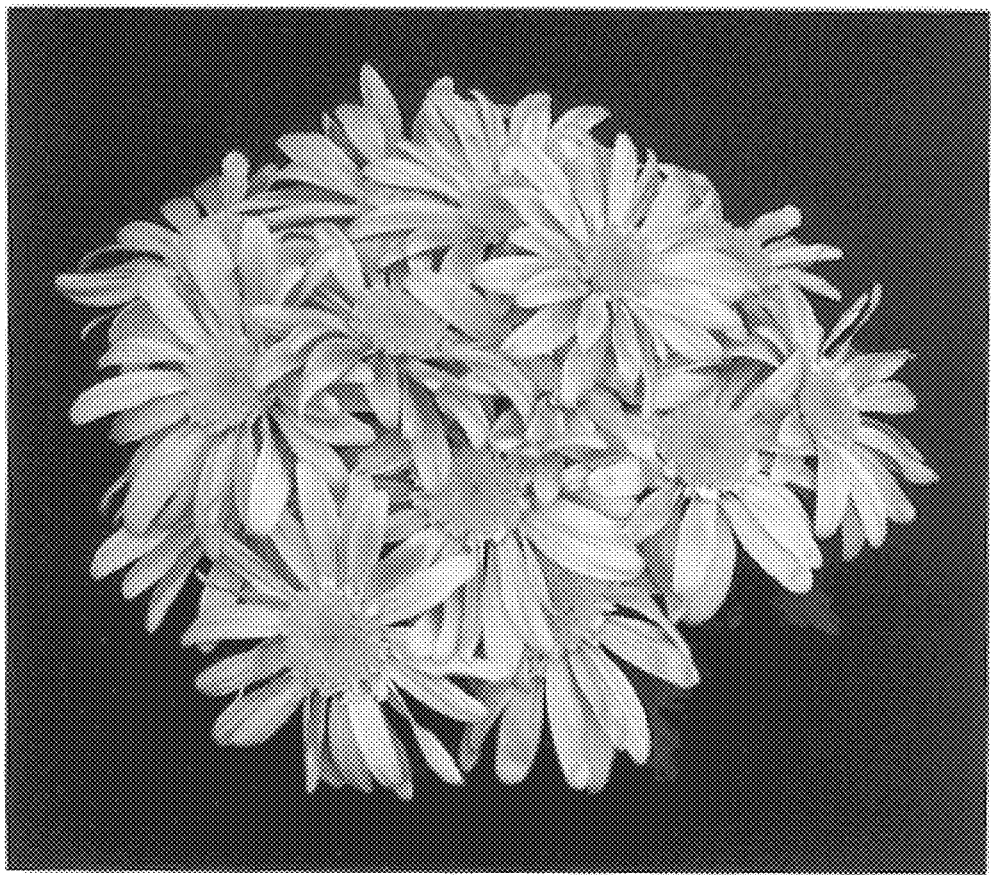

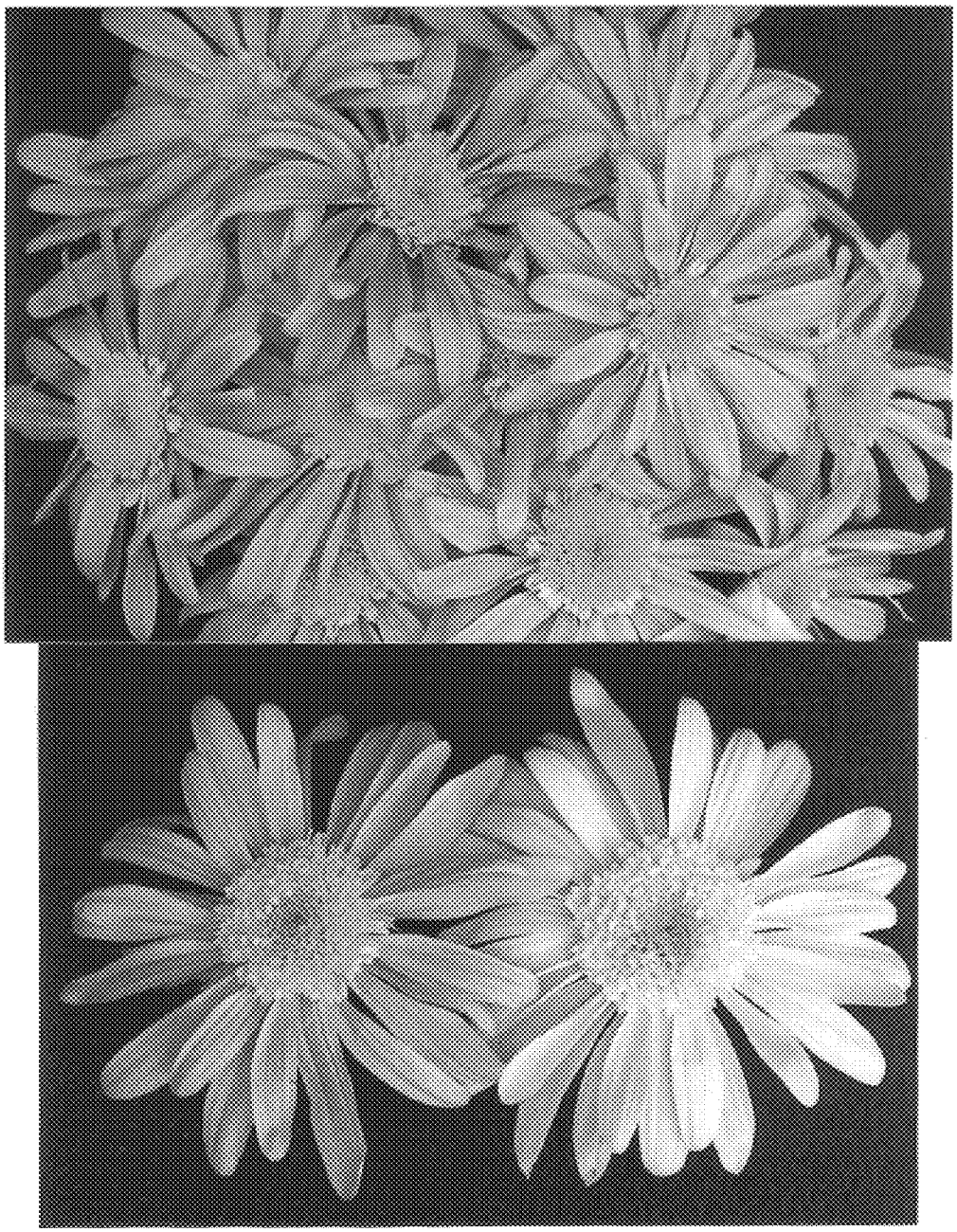

* * * * *